United States Patent [19]

Stein et al.

[11] 4,080,372

[45] Mar. 21, 1978

[54] CONTINUOUS PROCESS FOR BLEACHING ACID ALPHA-SULFO-FATTY ACID ESTERS

[75] Inventors: Werner Stein, Dusseldorf; Horst Baumann, Leichlingen; Hans Josef Rommerskirchen, Hilden, all of Germany

[73] Assignee: Henkel Kommanditgesellschaft auf Aktien (Henkel KGaA), Dusseldorf-Holthausen, Germany

[21] Appl. No.: 748,096

[22] Filed: Dec. 6, 1976

[30] Foreign Application Priority Data

Dec. 6, 1975 Germany ............................ 2555076

[51] Int. Cl.$^2$ ............................................. C07C 143/90
[52] U.S. Cl. ................................. 260/400; 260/423; 260/424
[58] Field of Search ...................... 260/400, 423, 424

[56] References Cited

U.S. PATENT DOCUMENTS

| | | | |
|---|---|---|---|
| 3,159,657 | 12/1964 | Wulff et al. | 260/400 |
| 3,354,187 | 11/1967 | Stein et al. | 260/400 |
| 3,452,064 | 6/1969 | Stein et al. | 260/400 |
| 3,485,856 | 12/1969 | Wulff et al. | 260/400 |
| 3,971,815 | 7/1976 | Sagel et al. | 260/400 |

Primary Examiner—Winston A. Douglas
Assistant Examiner—John F. Niebling
Attorney, Agent, or Firm—Hammond & Littell

[57] ABSTRACT

A continuous process for the bleaching of acid α-sulfo-fatty acid esters of predominantly $C_{16-24}$ fatty acids comprising continuously adding the hydrogen peroxide bleach in aqueous solution as well as from 2% to 50% by weight, based on the sulfonated esters, of a $C_{6-18}$ alkylbenzene sulfonic acid, to said raw, acid α-sulfo-fatty acid esters at a temperature of 40° to 65° C, continuously passing said mixture through a confined zone of dimensions sufficient to give a proper bleach retention time and continuously recovering bleached α-sulfo-fatty acid esters.

14 Claims, 1 Drawing Figure

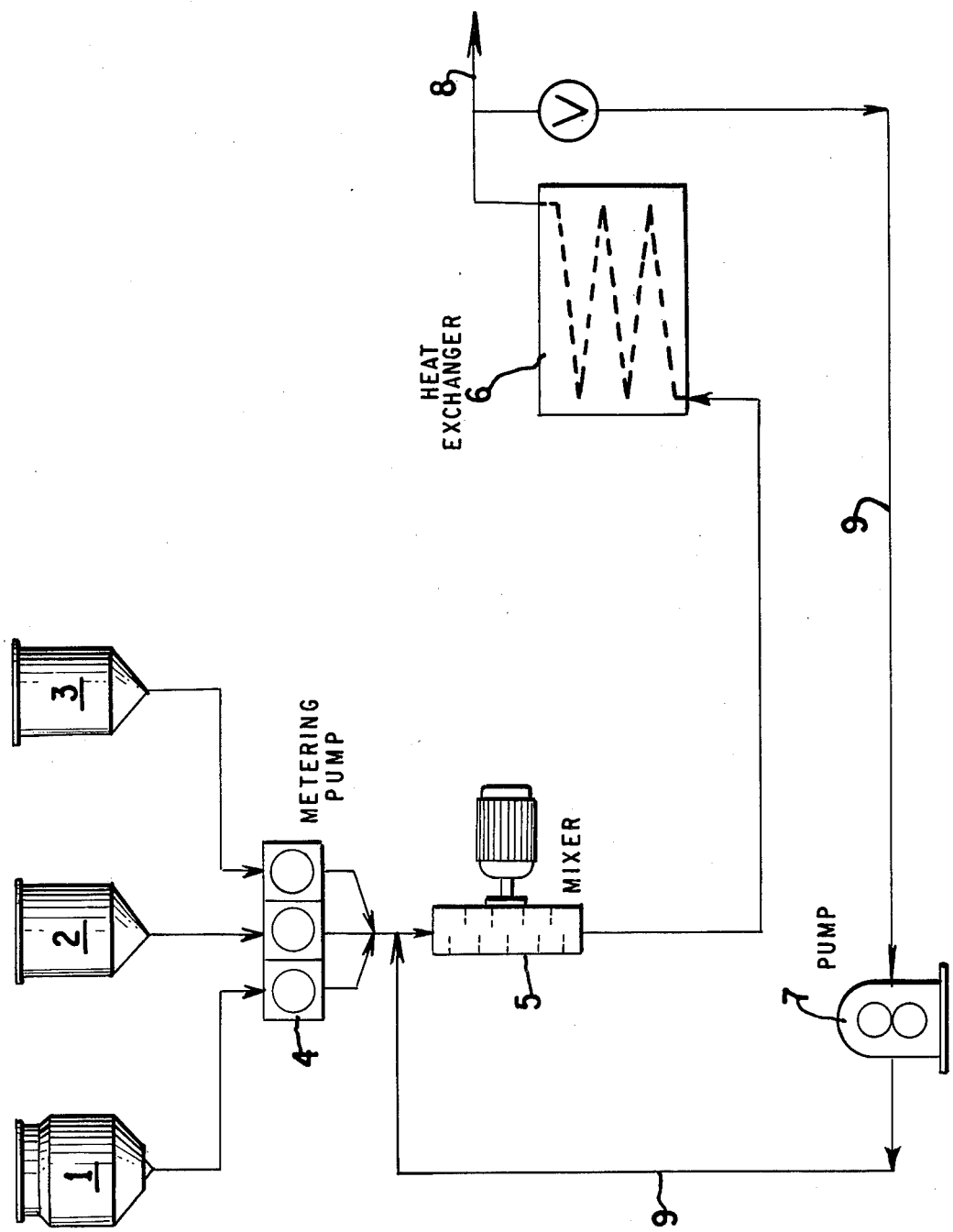

CONTINUOUS PROCESS FOR BLEACHING ACID ALPHA-SULFO-FATTY ACID ESTERS

The present invention relates to a continuous bleaching process for raw, acid α-sulfo-fatty acid esters with the addition of an alkylbenzene sulfonic acid and the use of an aqueous solution of hydrogen peroxide as a bleaching agent.

THE RELATED ART

When fatty acid esters are treated with gaseous sulfur trioxide diluted with an inert gas to produce acid α-sulfo-fatty acid esters, the sulfonation product is discolored. Austrian Patent Specification No. 239,770, corresponding to British Pat. No. 1,001,283, describes a process for the bleaching of α-sulfo-fatty acid esters which comprises using hydrogen peroxide, compounds forming hydrogen peroxide, or other inorganic bleaching agents having an oxidative action, to bleach, under specific working conditions, the acid sulfonic acids obtained by treating the fatty acid esters with gaseous sulfur trioxide diluted with inert gas in the absence of solvents. The disclosure of Austrian Pat. No. 239,770 and British Pat. No. 1,001,283 was filed in the United States as three applications, U.S. Pat. Nos. 3,159,657; 3,142,691 and 3,354,187. However, when attempting to put the process into practice, technical difficulties arose when the proportion of sulfo-fatty acid esters having 16 or more carbon atoms in the fatty acid component amounted to more than 70% in the mixture to be bleached. This is the case, for example, with the sulfo-fatty acid esters obtained from hydrogenated tallow fatty acid.

Owing to their melting or softening points, α-sulfo-fatty acid ester mixtures of this type must be maintained at temperatures of at least 40° C for the purpose of processing in continuous plant, in order to ensure the flowability of the sulfonic acids. If the desired quantity of hydrogen peroxide required for bleaching is now added in the form of an aqueous solution, the originally viscose but flowable and substantially homogeneous mass is converted into a non-homogeneous highly viscose product which is difficult to mix and which is virtually incapable of being pumped. Owing to the exothermic bleaching reaction which takes place, the non-homogeneous distribution of the hydrogen peroxide causes local overheating and thus the formation of colored impurities.

In order to overcome this difficulty, German patent specification No. 1,234,709 corresponding to U.S. Pat. No. 3,452,064, proposes a continuous multi-step bleaching process for acid products of sulfonation, namely, raw α-sulfo-fatty acid esters, at least 70% of whose fatty acids have a chain length of 16 and/or 18 carbon atoms. In the first bleaching stage of this process, the products of sulfonation are partially bleached by adding thereto a quantity of bleaching agent less than the quantity required for complete bleaching, particularly an aqueous solution of hydrogen peroxide. After subsequent neutralization, the neutralized, partially bleached sulfofatty acid esters are completely bleached in the second bleaching stage with further bleaching agent, particularly with hypochlorous acid or salts thereof.

However, problems arise in the practical realization of this multi-step bleaching process, since the quantity of bleaching agent to be metered in the first bleaching stage cannot be determined from the requirement for optimum bleaching, but is limited by the viscosity of the bleaching mixture. Thus, a continuous mode of operation is no longer possible with a slight over-dosage of the bleaching agent. A further disadvantage arises when, in accordance with a technically preferred embodiment of the process described in German patent specification No. 1,234,709, sodium hypochlorite is used in the second bleaching stage as the bleaching agent having an oxidative action. The neutralized and bleached sulfonate pastes then contain an increased salt concentration of sodium chloride, so that the products have a very high paste viscosity and are, therefore, difficult to handle.

OBJECTS OF THE INVENTION

Therefore, an object of the present invention is to develop a continuous process for the bleaching of raw, acid α-sulfo-fatty acid esters, a method which could be put into practice without the aforesaid disadvantages.

Another object of the present invention is the development of a continuous process for bleaching of acid α-sulfo-fatty acid esters comprising the steps of continuously mixing a mixture of (1) a raw acid α-sulfo-fatty acid ester wherein the fatty acid moiety of said ester contains at least 70% by weight of fatty acids having from 16 to 24 carbon atoms and the alcohol moiety of said ester is a member selected from the group consisting of alkanols having 1 to 3 carbon atoms, alkanediols having 2 to 3 carbon atoms and glycerine, and substantially all of the hydroxyl groups are esterified, said ester having a temperature of from above the flowability temperature to below 70° C, (2) from 1% to 5% by weight of said ester, of hydrogen peroxide on a 100% basis and added in the form of a 20% to 75% aqueous solution, and (3) from 2% to 50% by weight of said ester, of an alkylbenzene sulfonic acid having from 6 to 18 carbon atoms in the alkyl, continuously passing said mixture through a bleaching zone of dimensions and at such a rate to give the preselected bleach retention time, and continuously recovering bleached acid α-sulfo-fatty acid esters.

These and other objects of the invention will become more apparent as the description thereof proceeds.

THE DRAWING

The Drawing shows a flow diagram of the continuous bleaching process of the invention.

DESCRIPTION OF THE INVENTION

A continuous process has now been found for the bleaching of acid α-sulfo-fatty acid esters in which at least 70% of the fatty acid moieties present have a chain length of 16 to 24 carbon atoms and the alcoholic ester components can comprise monohydric or polyhydric alcohols having 1 to 3 carbon atoms, all the hydroxy groups having been esterified in the case of the polyvalent alcohols, by using 1% to 5% by weight of hydrogen peroxide calculated as 100% hydrogen peroxide with reference to the raw α-sulfo-fatty acid esters and used in the form of a 20% to 75% aqueous solution, the method being characterized in that a quantity of 2% to 50% by weight of an alkylbenzene sulfonic acid, whose side chain comprises 6 to 18 carbon atoms, is added prior to bleaching to the raw, acid α-sulfo-fatty acid esters at temperatures of from 40° to 65° C, which are then bleached.

More particularly, the invention relates to a continuous process for bleaching of acid α-sulfo-fatty acid esters comprising the steps of continuously mixing a mixture of (1) a raw acid α-sulfo-fatty acid ester wherein the fatty acid moiety of said ester contains at least 70% by weight of fatty acids having from 16 to 24 carbon atoms and the alcohol moiety of said ester is a member selected from the group consisting of alkanols having 1 to 3 carbon atoms, alkanediols having 2 to 3 carbon atoms and glycerine, and substantially all of the hydroxyl groups are esterified, said ester being maintained at a temperature of from above the flowability temperature to below 70° C, (2) from 1% to 5% by weight of said ester, of hydrogen peroxide on a 100% basis and added in the form of a 20% to 75% aqueous solution, and (3) from 2% to 50% by weight of said ester, of an alkylbenzene sulfonic acid having from 6 to 18 carbon atoms in the alkyl, continuously passing said mixture through a bleaching zone of dimensions and at such a rate to give the preselected bleach retention time, and continuously recovering bleached acid α-sulfo-fatty acid esters.

The minimum temperatures to be observed during the mixing steps or the addition, in accordance with the present invention, of alkylbenzene sulfonic acid are dependent upon the fatty acid composition of the acid α-sulfo-fatty acid esters used as a starting material. If fatty acids having a maximum of 14 carbon atoms, particularly fatty acids having 10 to 12 carbon atoms, are present in quantities of approximately 30% by weight, the product of the sulfonation softens at approximately 40° C and can be continuously processed at this temperature. The minimum temperatures increase as the number of carbons in the fatty acids increases. Advantageously, the alkylbenzene sulfonic acid is added at temperatures of at least 50° C to a sulfonic acid, 90% of whose fatty acids comprise $C_{16}$ and/or $C_{18}$ fatty acids, such as a sulfonic acid of the type derived from a hydrogenated tallow fatty acid ester. Before adding the bleaching agent, the aqueous solution of hydrogen peroxide, the temperature (of the sulfonic acid mixture) should, as far as possible, not exceed 70° C and, preferably should not exceed 65° C. The temperature of the mixture before addition of the aqueous hydrogen peroxide, therefore, should be above the flowability temperatures of the raw, acid α-sulfo-fatty acid ester and below 70° C.

The alkylbenzene sulfonic acids suitable for the addition to the bleaching process in accordance with the present invention include those which are produced by reacting an excess of benzene with an alkylation agent in the presence of a Friedel-Craft catalyst and subsequent sulfonation. Suitable alkylation agents are olefins, alcohols or halides which contain linear or branched chains having 6 to 18 carbon atoms. Preferably, the alkylbenzene sulfonic acids used in accordance with the present invention contain a linear alkyl chain. However, a technical alkylbenzene sulfonic acid mixture having linear side chains of 10 to 13 carbon atoms is preferred.

The quantity of alkylbenzene sulfonic acid added to the raw α-sulfo-fatty acid ester to be bleached lies between 2% and 50% by weight, preferably 3% to 25% by weight, particularly 3% and 15% by weight, with reference to the sulfonated fatty acid ester. It will be appreciated that the amount of alkylbenzene sulfonic acid suitable for reducing viscosity of the bleaching mixture depends upon the nature, particularly the chain length distribution, of the fatty acid components of the raw α-sulfo-fatty acid ester.

The concentration of the aqueous solution of the hydrogen peroxide used as a bleaching agnet has to be chosen such that, considered mathematically, the sulfuric acid, formed from the surplus sulfur trioxide present in the sulfonic acid and the water with which the bleaching agent is added, is no more dilute than a 60% by weight sulfuric acid. Products of sulfonation having a degree of sulfonation of at least 90%, preferably at least 96%, are obtained if, during the sulfonation of the fatty acid esters, the entire quantity of $SO_3$ required for sulfonation, which can lie in the range of 1.2 and 1.5 mol of $SO_3$ per mol of fatty acid moiety in the ester, is allowed to act upon the fatty acid ester at least for a time at temperatures above 70° C. As a result of this, the concentration of the aqueous solution of bleaching agent lies between 20% and 75% by weight, preferably between 30% and 40% by weight.

During the bleaching process, care has to be taken that the heat of reaction which occurs is dissipated by cooling and a bleaching temperature of less than 90° C, preferably from 55° to 75° C, is maintained.

It will be appreciated that the duration of the bleaching process depends upon the nature of the starting material, the quantity of the bleaching agent used and the bleaching temperature. It can vary within wide limits, although it generally lies between 5 minutes and 1 hour, preferably between 10 and 20 minutes. In the continuous process, the bleach time is selected and the bleach retention time in the bleaching zone is determined by the rate of input and output of the reactants.

After the bleaching process, the acid products can be neutralized in a known manner and converted to their salts. In addition to caustic soda, all other conventionally used inorganic or organic bases or basic salts can be used for neutralization, such as the other alkali metal hydroxides, for example, potassium hydroxide, alkali metal carbonate or bicarbonate, ammonia and primary, secondary or tertiary amines with lower alkyl or lower alkylol radicals, for example, methylamine and triethanolamine. The bases are employed in the form of an aqueous solution for the neutralization.

The bleaching process in accordance with the present invention is particularly suitable for a continuous mode of operation, since troublesome increases in viscosity during the bleaching operation are avoided by adding the alkylbenzene sulfonic acid to the raw acid α-sulfo-fatty acid ester product, and the products remain capable of being pumped throughout the bleaching.

By way of example, the process in accordance with the present invention can be carried out continuously in an apparatus as shown in the flow diagram of the drawing. The reservoir 1 contains the raw α-sulfo-fatty acid ester product to be bleached. This reservoir 1 is jacketed to maintain the ester at the desired temperature. Reservoirs 2 and 3 contain the alkylbenzene sulfonic acid to be added, and the aqueous bleaching agent. The three components are fed to a mixer 5 by means of a metering pump unit 4 which feeds the preselected amounts to mixer 5. The bleaching mixture comprising the raw acid product of sulfonation, the added alkylbenzene sulfonic acid and the aqueous solution of hydrogen peroxide reacts in a heat exchanger 6 from where it is pumped for neutralization 8. Advantageously, for improved dissipation of the heat of reaction, a portion of the bleached product is returned to the mixer 5 by means of line 9 and feed pump 7, wherein the ratio of bleached returned matter to unbleached sulfonic acid mixture can lie in the range of from 10:1 to 1:1.

The present invention will now be further illustrated by way of the following examples without, however, it being limited thereto.

EXAMPLES

If not stated otherwise, the bleaching tests described in the Examples were carried out in accordance with the following:

The required quantities of technical dodecylbenzene sulfonic acid (a linear side chain of a length distribution of approximately 5% by weight of $C_{10}$, approximately 42% by weight of $C_{11}$, approximately 37% by weight of $C_{12}$ and approximately 16% by weight of $C_{13}$) and 35% aqueous hydrogen peroxide solution were added to the raw product of sulfonation at temperatures of from 55° to 65° C. The bleaching temperature was maintained between 55° and 65° C by external cooling. Five minutes after adding the bleaching agent, the viscosity of the bleaching mixture at the bleaching temperature was determined in a rotary viscosimeter according to Brookfield. The bleached products were neutralized with aqeuous caustic soda after a total bleaching time of from 10 to 20 minutes. The color values of the neutralized products in a 5% by weight aqueous solution were subsequently determined by means of a "Lovibond Tintometer" in cuvettes having a thickness of 4 inches.

EXAMPLE 1

The starting raw material for the bleaching operation was the product of sulfonation of a hydrogenated tallow fatty acid methyl ester (chain length distribution of the fatty acids: approximately 32% $C_{16}$, approximately 65% $C_{18}$). The degree of sulfonation of the product was 98%. The viscosity values of the bleaching mixtures at 63° C after five minutes and the color values of the bleached products are given in Table 1 for various quantities of bleaching agent (calculated as 100% hydrogen peroxide with reference to the sulfonated ester) and technical dodecylbenzene sulfonic acid. It will be seen from the Table that the viscosity of the bleaching mixture was reduced to a considerable extent by adding only 3% by weight of alkylbenzene sulfonic acid (ABS). Furthermore, the viscosity is greatly dependent upon the quantity of bleaching agent (as $H_2O_2$) added.

TABLE 1

Results of the Bleaching Tests with Sulfonated Hardened Tallow Fatty Acid Methylester

| ABS (% by weight) | $H_2O_2$ (% by weight) | Viscosity (cP, 63° C) | Color Values | | |
|---|---|---|---|---|---|
| | | | Yellow | Red | Blue |
| 0 | 1.7 | 950 | 22 | 6 | 0 |
| 3 | 1.7 | 150 | 23 | 6.5 | 0 |
| 5 | 1.7 | 145 | 24 | 7 | 0 |
| 10 | 1.7 | 155 | 25 | 8 | 0 |
| 15 | 1.7 | 140 | 26 | 9 | 0 |
| 0 | 2.0 | 1400 | 11 | 3 | 0 |
| 3 | 2.0 | 260 | 12 | 3.2 | 0 |
| 5 | 2.0 | 170 | 12.5 | 3.4 | 0 |
| 10 | 2.0 | 160 | 14 | 3.8 | 0 |
| 15 | 2.0 | 165 | 17 | 4.4 | 0 |
| 0 | 2.5 | >10000 | 7 | 1.6 | 0 |
| 3 | 2.5 | 300 | 7.5 | 1.8 | 0 |
| 5 | 2.5 | 250 | 8 | 2.1 | 0 |
| 10 | 2.5 | 180 | 9 | 2.4 | 0 |
| 15 | 2.5 | 170 | 11 | 2.8 | 0 |

EXAMPLE 2

In another series of bleaching tests, the product of sulfonation of methyl stearate with a degree of sulfonation of 95.5% was bleached for approximately 15 minutes with the addition of technical dodecylbenzene sulfonic acid (A) and n-octylbenzenesulfonic acid (B) of uniform chain length, each with 2% by weight of hydrogen peroxide calculated as 100% $H_2O_2$ with reference to the sulfonated ester. The viscosity and color values of the products bleached at 65° C are given in Table 2.

TABLE 2

Results of the Bleaching Tests With Sulfonated Methyl Stearate

| ABS (% by weight) | Viscosity (cP, 65° C) | Color Values | | |
|---|---|---|---|---|
| | | Yellow | Red | Blue |
| 0 | >10,000 | 13 | 3.5 | 0 |
| 5 A | 450 | 15 | 3.8 | 0 |
| 10 A | 250 | 14 | 4.0 | 0 |
| 15 A | 150 | 20 | 5.0 | 0 |
| 5 B | 500 | 14 | 3.7 | 0 |
| 10 B | 300 | 15 | 3.9 | 0 |
| 15 B | 200 | 19 | 5.2 | 0 |
| 20 B | 190 | 25 | 8 | 0 |
| 30 B | 185 | 27 | 12 | 0 |

EXAMPLE 3

Table 3 gives the results of the bleaching tests with the product of the sulfonation of hardened rape oil fatty acid methyl ester, the hydrogenated rape oil fatty acids having a chain length distribution of approximately 10% $C_{16}$, approximately 40% $C_{18}$, approximately 10% $C_{20}$, and approximately 40% $C_{22}$ fatty acids. Different quantities of technical dodecylbenzene sulfonic acid (ABS) were added as the alkylbenzene sulfonic acid to the raw product of sulfonation (degree of sulfonation 98%) as well as 2% by weight of hydrogen peroxide calculated as 100% hydrogen peroxide with reference to the sulfonated ester.

TABLE 3

Bleaching of the Product of Sulfonation of a Hardened Rape Oil Fatty Acid Methyl Ester

| ABS (% by weight) | Viscosity (cP, 65° C) | Color Values | | |
|---|---|---|---|---|
| | | Yellow | Red | Blue |
| 0 | not measurable | 8 | 2.0 | 0 |
| 5 | >10,000 | 10 | 2.4 | 0 |
| 10 | 420 | 12 | 2.5 | 0 |
| 15 | 180 | 13 | 2.8 | 0 |

EXAMPLE 4

The bleaching mixtures of the product of sulfonation of hardened tallow fatty acid ethyl ester were also tested in addition to the α-sulfo-fatty acid methyl ester products. The product (degree of sulfonation 93.4%) was bleached with different additional quantities of technical dodecylbenzene sulfonic acid with the use of 3.5% by weight of $H_2O_2$ (calculated as 100% $H_2O_2$ with reference to the sulfonated fatty acid ester) in the form of a 40% aqueous solution. The bleaching temperature was 55° C. The results of the measurements are given in Table 4.

TABLE 4

Bleaching Tests on Raw, Acid α-Sulfo-Hydrogenated Tallow Fatty Acid Ethyl Ester

| ABS (% by weight) | Viscosity (cP, 55° C) | Color Values | | |
|---|---|---|---|---|
| | | Yellow | Red | Blue |
| 0 | 3,300 | 6 | 1.7 | 0 |
| 3 | 450 | 7 | 1.8 | 0 |
| 5 | 380 | 7 | 1.8 | 0 |
| 10 | 220 | 9 | 2.3 | 0 |

TABLE 4-continued

Bleaching Tests on Raw, Acid α-Sulfo-Hydrogenated Tallow Fatty Acid Ethyl Ester

| ABS (% by weight) | Viscosity (cP, 55° C) | Color Values | | |
|---|---|---|---|---|
| | | Yellow | Red | Blue |
| 15 | 190 | 12 | 2.8 | 0 |

EXAMPLE 5

43.2 kg (150 mol)/hour of hydrogenated tallow fatty acid methyl ester were continuously reacted with 13.8 kg (172.5 mol)/hour of $SO_3$ in the form of an approximately 5% by volume mixture with air, in a reactor at a circulating water temperature of 90° C. After passing through a secondary reaction container heated to 90° C (average dwell time: 20 minutes) and a cooling bath, the 57 kg products of sulfonation (degree of sulfonation 95.6%) yielded hourly were continuously mixed in a mixer with 4.07 kg ≙ 3.5 liter/hour of a 35% by weight $H_2O_2$ solution (2.5% by weight of 100% $H_2O_2$, with reference to the sulfonated ester) at a temperature of 50° to 55° C and, for the purpose of bleaching, were subsequently pumped through a serpentine pipe provided with a cooling jacket. The serpentine pipe was dimensioned such that a dwell time of approximately 15 minutes resulted. The bleaching temperature was kept at 60° to 65° C by cooling with 50° to 55° C hot water. The pressure increased rapidly in excess of 10 atmospheres gauge pressure a short time after mixing the first sulfonated ester with the aqueous $H_2O_2$, so that the test had to be terminated. The bleaching mixture in the serpentine pipe had solidified to a highly viscose pulpy mass which was no longer capable of being pumped.

The test was repeated, however, in addition to the above-mentioned quantity of $H_2O_2$, 4 kg/hour of the technical dodecylbenzene sulfonic acid (7% by weight with reference to the sulfonated ester) was continuously mixed in the mixer. A pressure of approximately 1.5 atmospheres gauge pressure was established in the serpentine pipe at a bleaching temperature of 63° C. The bleaching mixture was highly fluid and could be pumped through the serpentine pipe without difficulty. A viscosity of 200 cP was measured in a sample of the bleaching mxiture in the rotary viscosimeter according to Brookfield. The bleached product was subsequently neutralized with a 7.5% by weight aqueous caustic soda at 40° to 45° C, resulting in a 28% by weight aqueous paste of sodium α-sulfohydrogenated tallow fatty acid methyl ester and sodium dodecylbenzene sulfonate. The color values of a 5% by weight solution, measured in the Lovibond Tintometer were:

Yellow - 6
Red - 1.4
Blue - 0

The preceding specific embodiments are illustrative of the practice of the invention. It is to be understood, however, tht other expedients known to those skilled in the art or disclosed herein may be employed without departing from the spirit of the invention or the scope of the appended claims.

We claim:

1. A continuous process for bleaching of acid α-sulfo-fatty acid esters comprising the steps of continuously mixing a mixture of
   (1) a raw acid α-sulfo-fatty acid ester wherein the fatty acid moiety of said ester contains at least 70% by weight of fatty acids having from 16 to 24 carbon atoms and the alcohol moiety of said ester is a member selected from the group consisting of alkanols having 1 to 3 carbon atoms, alkanediols having 2 to 3 carbon atoms and glycerine, and substantially all of the hydroxyl groups are esterified, said ester being maintained at a temperature of from above the flowability temperature to below 70° C,
   (2) from 1% to 5% by weight of said ester, of hydrogen peroxide on a 100% basis and added in the form of a 20% to 75% aqueous solution, and
   (3) from 2% to 50% by weight of said ester of an alkylbenzene sulfonic acid having from 6 to 18 carbon atoms in the alkyl,
continuously passing said mixture through a bleaching zone of dimensions and at such a rate to give the preselected bleach retention time, and continuously recovering bleached acid α-sulfo-fatty acid esters.

2. The process of claim 1 wherein said ester is maintained at a temperature of from 40° to 65° C.

3. The process of claim 1 wherein said alkylbenzene sulfonic acid has from 10 to 13 carbon atoms in the linear alkyl.

4. The process of claim 1 wherein said alkylbenzene sulfonic acid is added in amounts of from 3% to 25% by weight based on the raw acid α-sulfo-fatty acid ester.

5. The process of claim wherein said alkylbenzene sulfonic acid is added in amounts of from 3% to 15% by weight based on the raw acid α-sulfo-fatty acid ester.

6. The process of claim 1 wherein said raw acid α-sulfo-fatty acid ester has a degree of sulfonation of at least 90%.

7. The process of claim 1 wherein said raw acid α-sulfo-fatty acid ester has a degree of sulfonation of at least 96%.

8. The process of claim 1 wherein the amount of water added with said hydrogen peroxide is such that the surplus sulfur trioxide present in said raw acid ester will form with the water an at least 60% by weight sulfuric acid solution.

9. The process of claim 1 wherein said bleaching zone is cooled in order to maintain the beaching temperature at less than 90° C.

10. The process of claim 1 wherein said bleaching zone is cooled in order to maintain the bleaching temperature from 55° to 75° C.

11. The process of claim 1 wherein said bleach retention time is from 5 minutes to 1 hour.

12. The process of claim 1 wherein said bleach retention time is from 10 minutes to 20 minutes.

13. The process of claim 1 wherein part of said recovered bleached acid α-sulfo-fatty acid esters are recycled to said mixing step where the ratio of bleached returned ester to unbleached raw ester is from 10:1 to 1:1.

14. The bleached acid α-sulfo-fatty acid esters containing alkylbenzene sulfonic acid produced by the process of claim 1.

* * * * *

UNITED STATES PATENT OFFICE
CERTIFICATE OF CORRECTION

Patent No. 4,080,372　　　　　　　　　　Dated Mar. 21, 1978

Inventor(s) Werner Stein et al

It is certified that error appears in the above-identified patent and that said Letters Patent are hereby corrected as shown below:

Column 8, line 32, after "Claim" insert -- 1 --.

Signed and Sealed this

Eighth Day of August 1978

[SEAL]

Attest:

RUTH C. MASON
*Attesting Officer*

DONALD W. BANNER
*Commissioner of Patents and Trademarks*